(12) United States Patent
Allard et al.

(10) Patent No.: US 8,083,798 B2
(45) Date of Patent: Dec. 27, 2011

(54) NON-CIRCULAR STABILIZATION SPHERE AND METHOD

(75) Inventors: Randall N. Allard, Germantown, TN (US); Robert B. Rice, Southaven, MS (US); Mark C. Dace, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 257 days.

(21) Appl. No.: 11/098,167

(22) Filed: Apr. 4, 2005

(65) Prior Publication Data

US 2006/0224240 A1  Oct. 5, 2006

(51) Int. Cl.
*A61F 2/44* (2006.01)

(52) U.S. Cl. ............ 623/17.16; 623/17.14; 606/90

(58) Field of Classification Search .... 623/17.11–17.16; 606/99, 246, 249, 914
See application file for complete search history.

(56) References Cited

U.S. PATENT DOCUMENTS

| | | | | |
|---|---|---|---|---|
| 4,714,469 A * | 12/1987 | Kenna | | 606/86 A |
| 4,936,848 A | 6/1990 | Bagby | | |
| 5,026,392 A * | 6/1991 | Gordon | | 623/6.64 |
| 5,059,193 A | 10/1991 | Kuslich | | |
| 5,431,657 A * | 7/1995 | Rohr | | 606/91 |
| 5,466,259 A * | 11/1995 | Durette | | 623/6.64 |
| 5,645,596 A | 7/1997 | Kim et al. | | |
| 5,653,761 A * | 8/1997 | Pisharodi | | 606/86 A |
| 5,743,918 A | 4/1998 | Calandruccio et al. | | |
| 5,888,226 A * | 3/1999 | Rogozinski | | 623/17.16 |
| 6,245,074 B1 * | 6/2001 | Allard et al. | | 606/80 |
| 6,299,642 B1 * | 10/2001 | Chan | | 623/16.11 |
| 6,319,257 B1 * | 11/2001 | Carignan et al. | | 606/99 |
| 6,391,058 B1 * | 5/2002 | Kuslich et al. | | 623/17.11 |
| 6,478,822 B1 | 11/2002 | Leroux et al. | | |
| 6,641,613 B2 * | 11/2003 | Sennett | | 623/17.11 |
| 7,001,433 B2 * | 2/2006 | Songer et al. | | 623/17.16 |
| 7,101,375 B2 * | 9/2006 | Zucherman et al. | | 606/249 |
| 7,105,023 B2 * | 9/2006 | Eckman | | 623/17.11 |
| 7,806,933 B2 * | 10/2010 | Sears et al. | | 623/17.11 |
| 2001/0012938 A1 * | 8/2001 | Zucherman et al. | | 606/61 |
| 2002/0156528 A1 | 10/2002 | Gau | | |
| 2003/0023308 A1 | 1/2003 | Leroux et al. | | |

(Continued)

FOREIGN PATENT DOCUMENTS

CA  2441384 A1  11/2002

(Continued)

OTHER PUBLICATIONS http://dictionary.reference.com, definition for "sphere", accessed on Jan. 25, 2010.* "Satellite Interdiscal Stabilization Sphere Surgical Technique" product pamphlet, Medtronic Sofamor Danek. 2004.

*Primary Examiner* — Eduardo C Robert
*Assistant Examiner* — Jan Christopher Merene

(57) ABSTRACT

A spacer for inserting between vertebral members. The spacer has a non-spherical shape with an anterior section having a first shape and a posterior section having a different shape. An attachment means is positioned within the posterior section, and may include a receiver for attachment with an insertion device, and an anti-rotation mechanism for assistance in removing the spacer from the insertion device. Embodiments of using the spacer is also disclosed which may include inserting the spacer between the vertebral members in a generally posterior approach. Once inserted, the insertion device acts with the anti-rotation device to remove a connection mechanism from the receiver. The spacer remains between the vertebral members and provides relief to the patient.

16 Claims, 7 Drawing Sheets

U.S. PATENT DOCUMENTS

| | | | |
|---|---|---|---|
| 2003/0074071 A1* | 4/2003 | Errico et al. | 623/17.14 |
| 2003/0074073 A1* | 4/2003 | Errico et al. | 623/17.14 |
| 2003/0135276 A1* | 7/2003 | Eckman | 623/17.11 |
| 2003/0204261 A1 | 10/2003 | Eisermann et al. | |
| 2003/0220691 A1* | 11/2003 | Songer et al. | 623/17.14 |
| 2004/0024461 A1 | 2/2004 | Ferree | |
| 2004/0030391 A1 | 2/2004 | Ferree | |
| 2004/0093082 A1 | 5/2004 | Ferree | |
| 2004/0181282 A1* | 9/2004 | Zucherman et al. | 623/17.11 |
| 2004/0186576 A1 | 9/2004 | Biscup et al. | |
| 2010/0185287 A1* | 7/2010 | Allard et al. | 623/17.11 |

FOREIGN PATENT DOCUMENTS

| | | |
|---|---|---|
| EP | 1328218 A | 7/2003 |
| EP | 1354572 A2 | 10/2003 |
| FR | 2 829 689 A | 3/2003 |
| WO | 9531948 | 11/1995 |
| WO | 0234169 A2 | 5/2002 |
| WO | 02087480 A1 | 11/2002 |
| WO | 03024368 A1 | 3/2003 |
| WO | 03099172 A1 | 12/2003 |

* cited by examiner

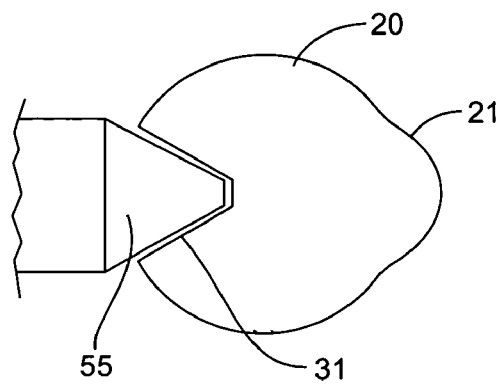
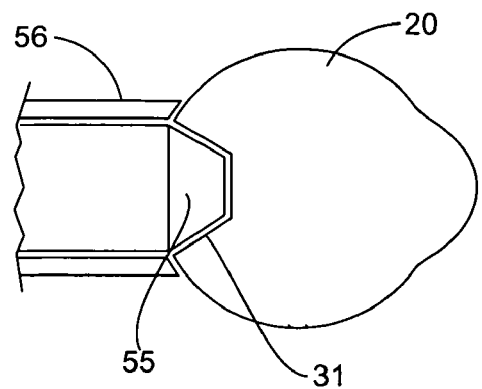
FIG. 18                FIG. 19
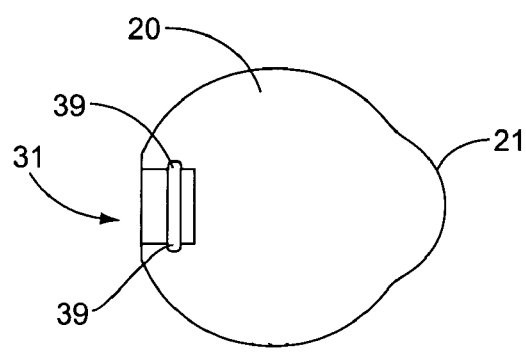
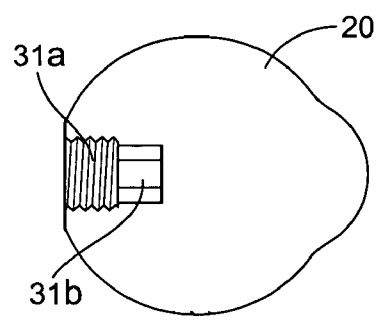
FIG. 20                FIG. 21

NON-CIRCULAR STABILIZATION SPHERE AND METHOD

BACKGROUND

The human spine is a biomechanical structure consisting of thirty-three vertebral members and is responsible for protecting the spinal cord, nerve roots and internal organs of the thorax and abdomen. The spine also provides structural support for the body while permitting flexibility of motion. A large majority of the population will experience back pain at some point in their lives that results from a spinal condition. The pain may range from general discomfort to disabling pain that immobilizes the individual. The back pain may result from a trauma to the spine, be caused by the natural aging process, or may be the result of a degenerative disease or condition.

Procedures to remedy these problems may require correcting the distance between vertebral members by inserting a spacer. The spacer is carefully positioned within the disc space and aligned relative to the vertebral members. The spacer is sized to position the vertebral members in a manner to alleviate the back pain.

The spacer may be designed to facilitate insertion into the body. The shape and size provide for minimal intrusion to the patient during insertion, but still be effective post-insertion to alleviate the pain and provide for a maximum of mobility to the patient.

The spacer may also provide for attachment with an insertion device to position the spacer within the body. The attachment should be of adequate strength for the insertion device to accurately insert and place the spacer. Further, the attachment should provide for detachment to remove the insertion device while the spacer remains within the body. The attachment further should not deter from the functionality of the member to be used within the body.

SUMMARY

An embodiment of the present invention is directed to a spacer that is positioned within the body. One embodiment features a first section having a spherical shape, and a second section extending outward from the first section in a first direction. An attachment feature may be positioned on the first section for attachment with an insertion device. Further, an anti-rotation feature may be positioned adjacent to the attachment feature to facilitate removal of the insertion device. The non-spherical shape of the spacer provides for alignment within the vertebral space, and prevents the attachment mechanism from contacting the vertebral members.

BRIEF DESCRIPTION OF THE DRAWINGS

FIG. 18 is a side schematic view of an insertion device and spacer according to one embodiment of the present invention;

FIG. 19 is a side schematic view of an insertion device and spacer according to one embodiment of the present invention;

FIG. 20 is a side is a side schematic view of a spacer according to one embodiment of the present invention; and FIG. 21 is a side schematic view of a spacer according to one embodiment of the present invention.

DETAILED DESCRIPTION

Figure 1:
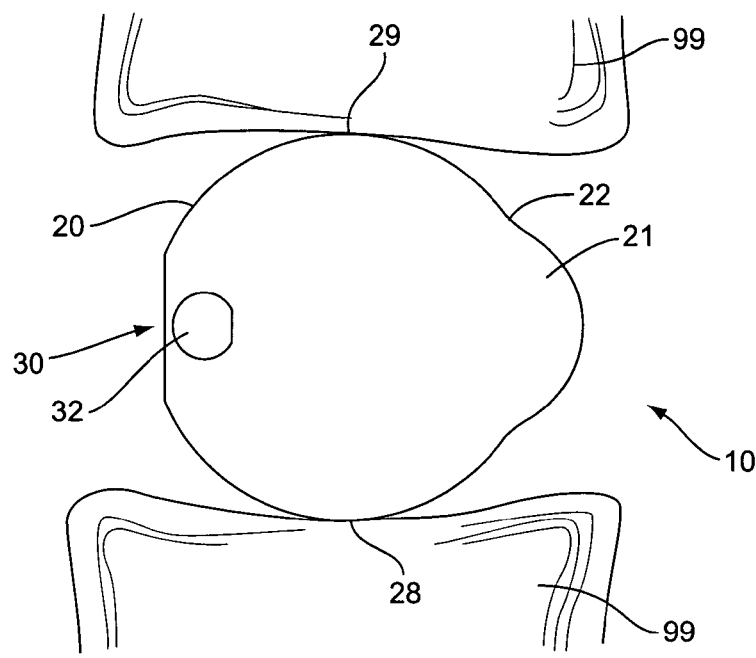
FIG. 1 is a side view of a spacer positioned between two vertebral members according to one embodiment of the present invention.
Figure 1A:
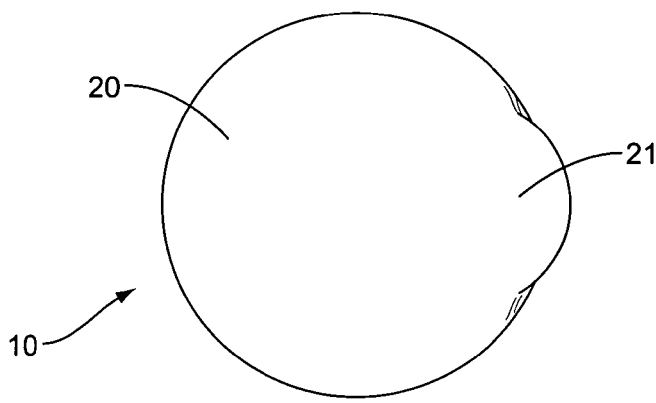
FIG. 1A is a perspective view of the spacer of FIG. 1 according to one embodiment of the present invention.

An embodiment of the present invention is directed to a spacer, generally illustrated as 10 in FIG. 1, for inserting between first and second vertebral members 99. The spacer 10 has an overall non-spherical shape comprised of a first section 20 and a second section 21. The first and second sections 20, 21 are arranged in an overlapping orientation to give the spacer 10 the overall non-spherical shape. An attachment feature 30 may be located within one of first and second sections 20, 21. The attachment feature 30 is located on the non-spherical spacer 10 at a position to remain spaced away from and avoid contact with the vertebral members 99.

Figure 2:
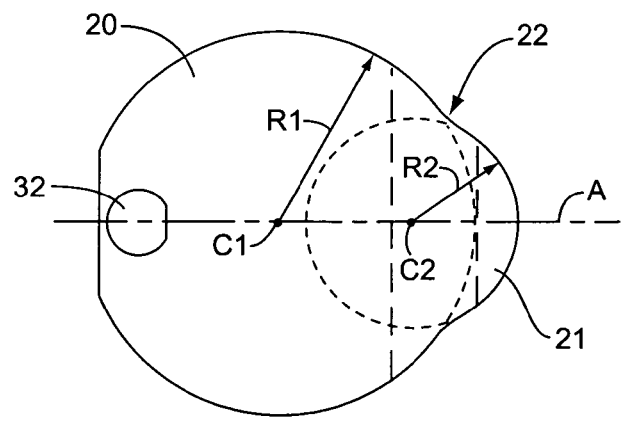
FIG. 2 is a side schematic view of a spacer of FIGS. 1 and 2 according to one embodiment of the present invention.

The spacer 10 of a first embodiment illustrated in FIG. 1 has an overall non-spherical shape comprised of a first section 20 and a second section 21. The non-spherical shape maintains the orientation of the spacer 10 with the inferior 28 and superior 29 surfaces in contact with the vertebral members 99. FIG. 2 illustrates a schematic view of the spacer 10 of the first embodiment. The first section 20 forms a majority of the spacer 10 and has a larger surface area than the second section 21. The first section 20 is substantially spherical having a radius R1 that extends from a center point C1. The second section 21 extends outward in a first direction from the first section 20. In this embodiment, the second section 21 is positioned on the anterior side of the first section 20. The second section 21 is substantially spherical having a radius R2 that extends from a center point C2. Both center points C1 and C2 are aligned along a common centerline A.

FIG. 2 illustrates the exterior surface of the spacer 10 in solid lines. The dashed lines illustrate the overlapping area between the first and second sections 20, 21. In one embodiment, the first and second sections 20, 21 are aligned with an overall length of the spacer 10 being about 9.6 mm.

Figure 10:
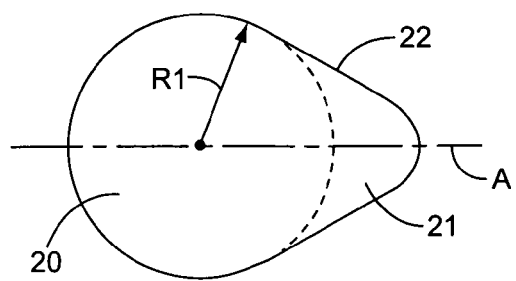
FIG. 10 is a side schematic view of a spacer according to one embodiment of the present invention.
Figure 11:
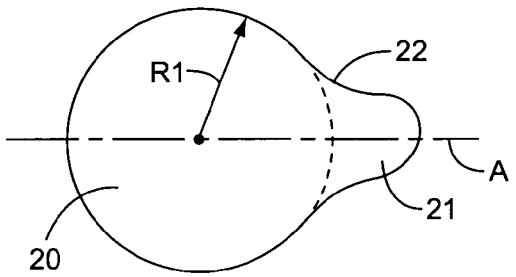
FIG. 11 is a side schematic view of a spacer according to one embodiment of the present invention.

A transition section 22 is positioned along an area where the exterior surface of the first section 20 merges with the exterior surface of the second section 21 as illustrated in FIG. 2. The protrusion of the second section 21 with respect to the first section 20 may cause the transition section 22 to be convex as illustrated in FIG. 2, tangent as illustrated in FIG. 10, or concave as illustrated in FIG. 11.

Figure 3:
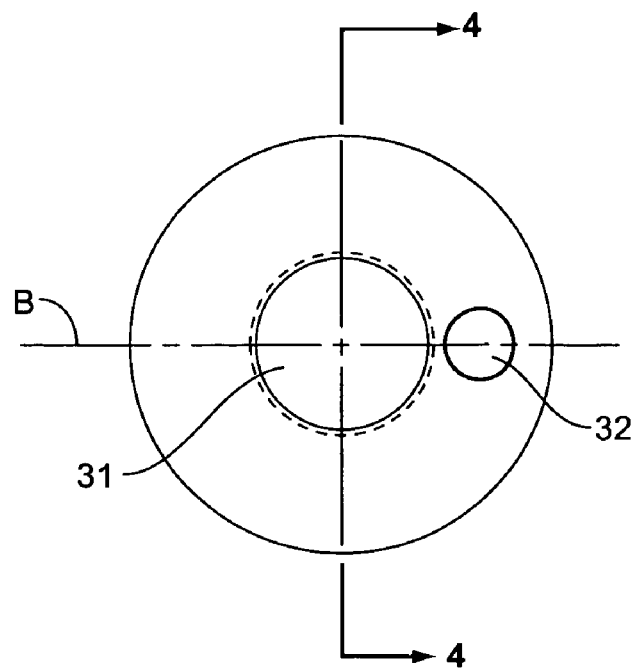
FIG. 3 is a rear view of a spacer of FIGS. 1 and 2 illustrating the attachment feature and anti-rotation feature on a first section according to one embodiment of the present invention.

The attachment means 30 includes a receiver 31 for mounting the insertion device 50. As illustrated in the embodiment of FIG. 3, the receiver 31 comprises an opening that is centered on the longitudinal centerline A and a lateral centerline B within the spacer 10. The opening 31 may include threads for attachment to the insertion device 50. In one embodiment, the depth of the receiver opening 31 is about 3.7 mm. An anti-rotation feature 32 may also be positioned in proximity to the attachment means 30. The anti-rotation feature 32 interacts with the insertion device 50 to facilitate removal of the spacer 10. The anti-rotation feature 32 provides a counter torque for the forces applied by the insertion device 50 during removal from the receiver 31. The anti-rotation feature 32 provides leverage for removing the insertion device 30. In the embodiment of FIG. 3, the feature 32 includes an opening that extends into the spacer 10 and is spaced away from the receiver opening 31. The attachment feature 30 is positioned on the spacer 10 to remain spaced away from the vertebral members 99. In the embodiment of FIG. 1, the attachment feature 30 is located on the posterior section of the spacer 10. The non-spherical shape of the spacer 10 maintains the superior 29 and inferior 28 surfaces of the first section 20 in contact with the vertebral members 99, and the attachment feature 30 spaced away from the vertebral members 99. In the event of a larger degree of rotation of the spacer 10 and using the embodiment of FIG. 1 as an example, when the spacer 10 rotates in a first direction (clockwise), a lower surface of the second section 21 contacts the lower vertebral member to prevent contact of the attachment feature 30 with the upper vertebral member. When the spacer 10 rotates in a second direction (counter-clockwise), an upper surface of the second section 21 contacts the upper vertebral member to prevent contact of the attachment feature 30 with the lower vertebral member. The edges of the attachment feature 30 may cause damage if placed in contact with the vertebral members 99.

Figure 5:
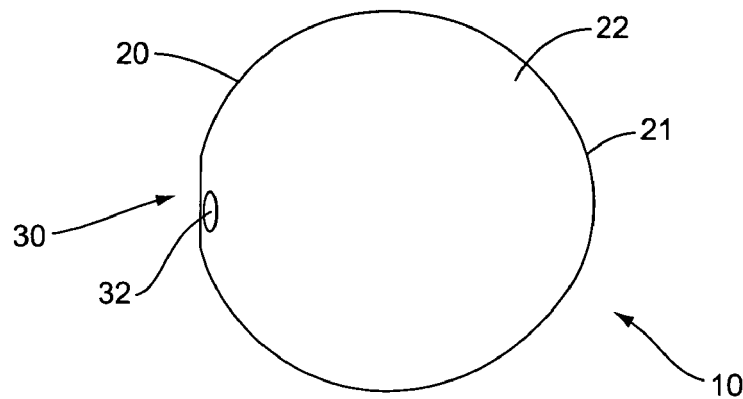
FIG. 5 is a side view of a spacer according to one embodiment of the present invention.
Figure 6:
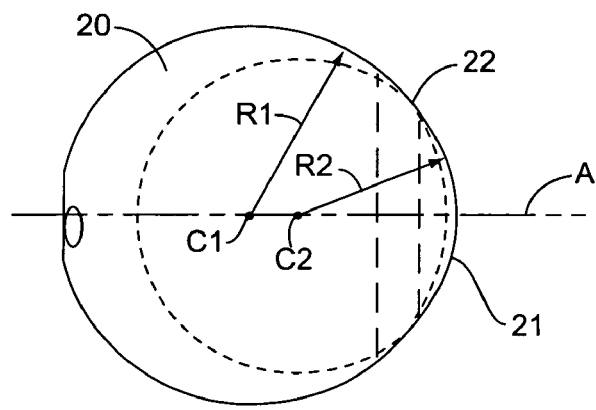
FIG. 6 is a side schematic view of the spacer of FIG. 5 according to one embodiment of the present invention.
Figure 7:
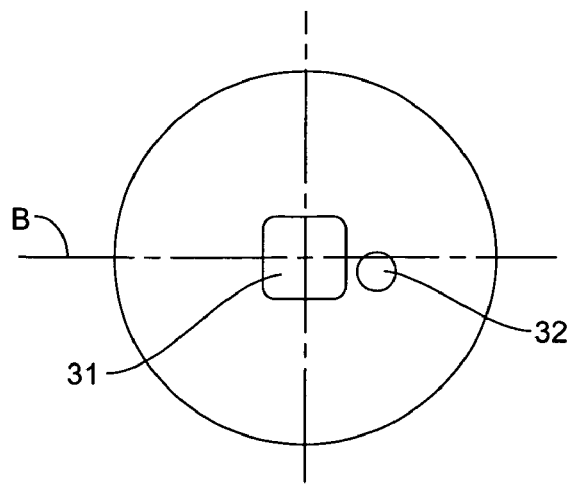
FIG. 7 is a rear view of a spacer of FIG. 5 illustrating the attachment feature and anti-rotation feature on the first section according to one embodiment of the present invention.

FIGS. 5, 6, and 7 illustrate another embodiment of the spacer 10. The spacer 10 again includes a first section 20, second section 21, and transition section 22. The first section 20 is substantially spherical having a radius R1 about a center point C1. The second section 21 is also substantially spherical having a radius R2 about a center point C2. The transition section 22 forms a continuous exterior surface between the first and second sections 20, 21. As illustrated in the embodiment of FIGS. 5 and 6, the second section 21 is less pronounced relative to the first section 20. This is caused by the similarities in size between the (i.e., closer radius R1 and R2), and the proximity of the center points C1, C2.

The attachment feature 30 is positioned on the first section 20 at a location to be spaced away from the vertebral members 99 and comprises a receiver opening 31 having a rectangular shape. An anti-rotation mechanism 32 comprising an opening is also positioned in proximity to the attachment feature 30. Each of the openings 31, 32 extend into the spacer 10 a predetermined distance, with the receiver opening 31 extending a greater distance. As illustrated in FIG. 6, the centerline A extends through the middle of the receiver opening 31, and also the center points C1, C2 of the first and second sections 20, 21. In this embodiment, opening 32 is offset from the centerline B.

Figure 8:
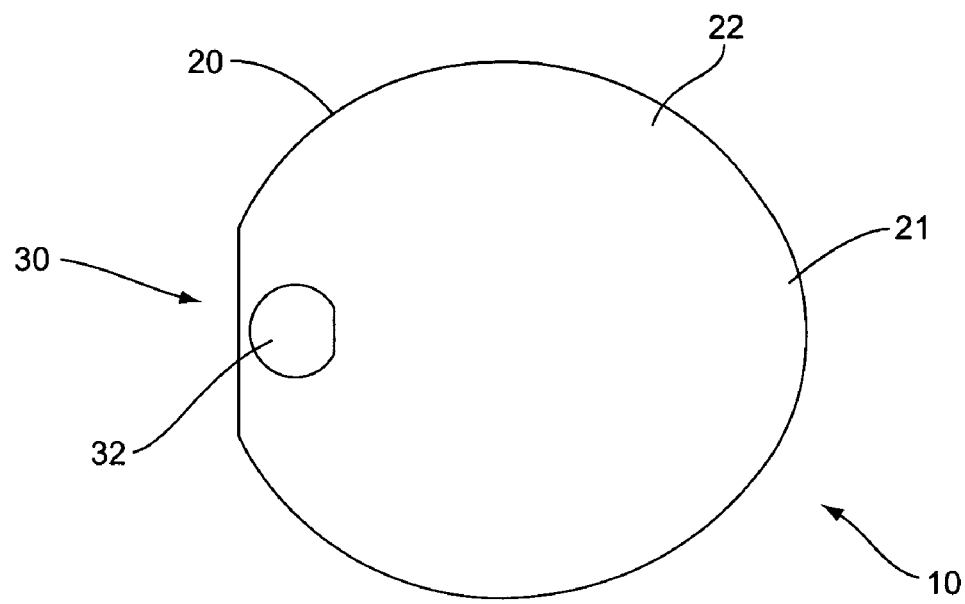
FIG. 8 is a side view of a spacer according to one embodiment of the present invention.
Figure 9:
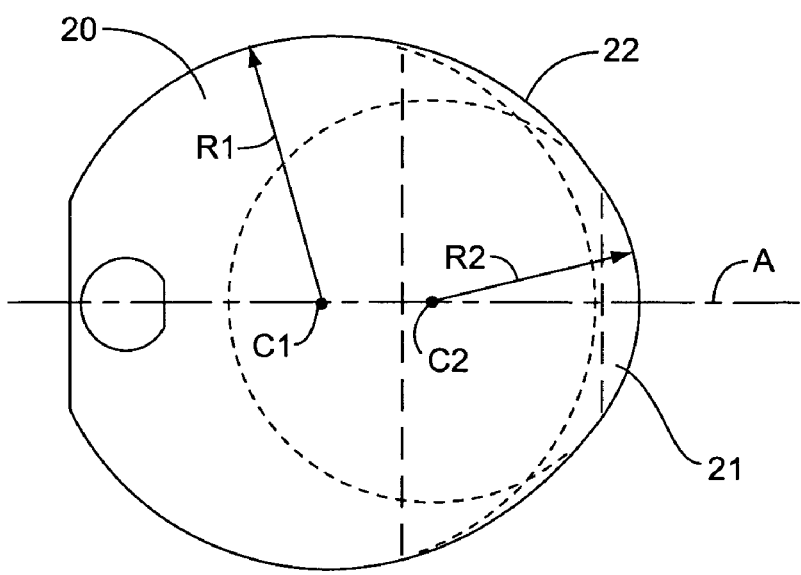
FIG. 9 is a side schematic view of the spacer of FIG. 8 according to one embodiment of the present invention.

FIGS. 8 and 9 illustrate another embodiment of a spacer 10 having a first section 20 and a second section 21, and transition section 22. The first section 20 has a center point C1 positioned along the centerline A and a radius R1. The second section 21 has a center point C2 positioned along the centerline A and a radius R2.

Each of the embodiments disclosed includes the attachment feature 30 and anti-rotation aspect 32 positioned within a posterior section of the spacer 10. This placement provides for a posterior insertion approach. It is to be understood that these elements may also be positioned at other locations on the spacer 10, such as in an anterior section for an anterior insertion approach, or along a lateral edge for a lateral approach. In each embodiment, the position of these elements is such that it is spaced from the vertebral members 99 to prevent damage.

FIG. 10 illustrates an embodiment having a substantially tangent transition section 22. The first section 20 is substantially spherical having a radius R1 positioned along a centerline A. The second section 21 extends outward from a first side of the first section 20. In this embodiment, second section 21 is centered relative to the centerline A. The transition section 22 extends in a substantially tangent manner from the first section 20.

Figure 12:
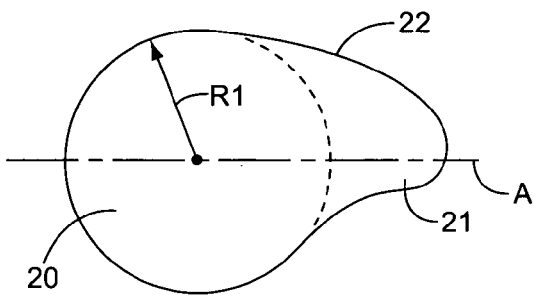
FIG. 12 is a side schematic view of a spacer according to one embodiment of the present invention.

FIG. 11 illustrates another embodiment having a concave transition section 22. FIG. 12 is an embodiment having a combined transitional section 22. An upper transitional section has a convex shape, and a lower transitional section has a concave shape. The orientation and curvature of the transition section 22 can vary depending upon the application.

Figure 14:
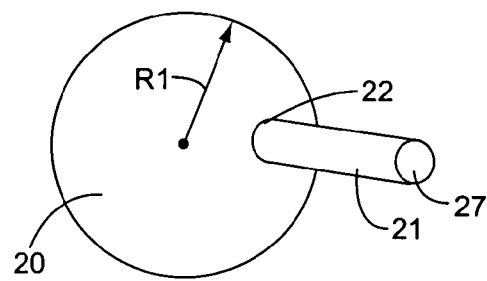
FIG. 14 is a perspective view of a spacer according to one embodiment of the present invention.
Figure 15:
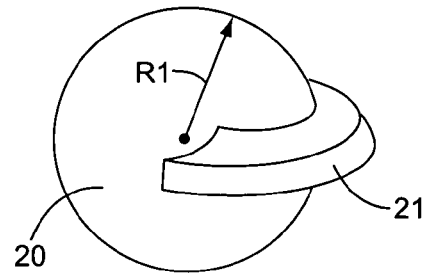
FIG. 15 is a perspective view of a spacer according to one embodiment of the present invention.
Figure 13:
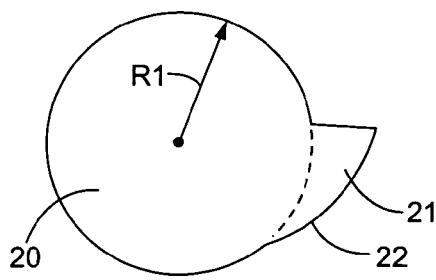
FIG. 13 is a side schematic view of a spacer according to one embodiment of the present invention.

The shapes and sizes of the second section 21 that extend from a side of the first section 20 can vary as necessary. FIG. 13 illustrates a second section 21 having a combined configuration. The upper transition section 22 has a stepped configuration, as the lower transition section has a convex orientation. FIG. 14 illustrates the second section 21 extending outward from a side of the first section 20 and having a cylindrical shape with an end 27 opposite from the first section 20. FIG. 15 illustrates an embodiment having a rim flange forming the second section 21 and extending from a side of the first section 20. The second section 21 has a small thickness that tapers at the ends to merge into the spherical shape of the first section 20.

Figure 16:
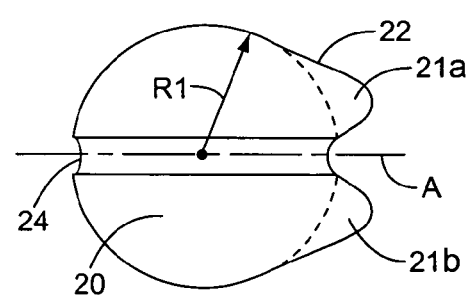
FIG. 16 is a side schematic view of a spacer according to one embodiment of the present invention.

FIG. 16 illustrates another embodiment having a groove 24 that extends around a spherical first section 20. The groove 24 may have different depths depending upon the application. The groove 24 in the embodiment of FIG. 16 is centered along the centerline A. The second section 21 comprises first and second extensions 21a, 21b that extend outward from a side of the first section 20. The first section 21a is positioned above the groove 24, and the second section 21b is positioned below the groove 24.

Figure 17:
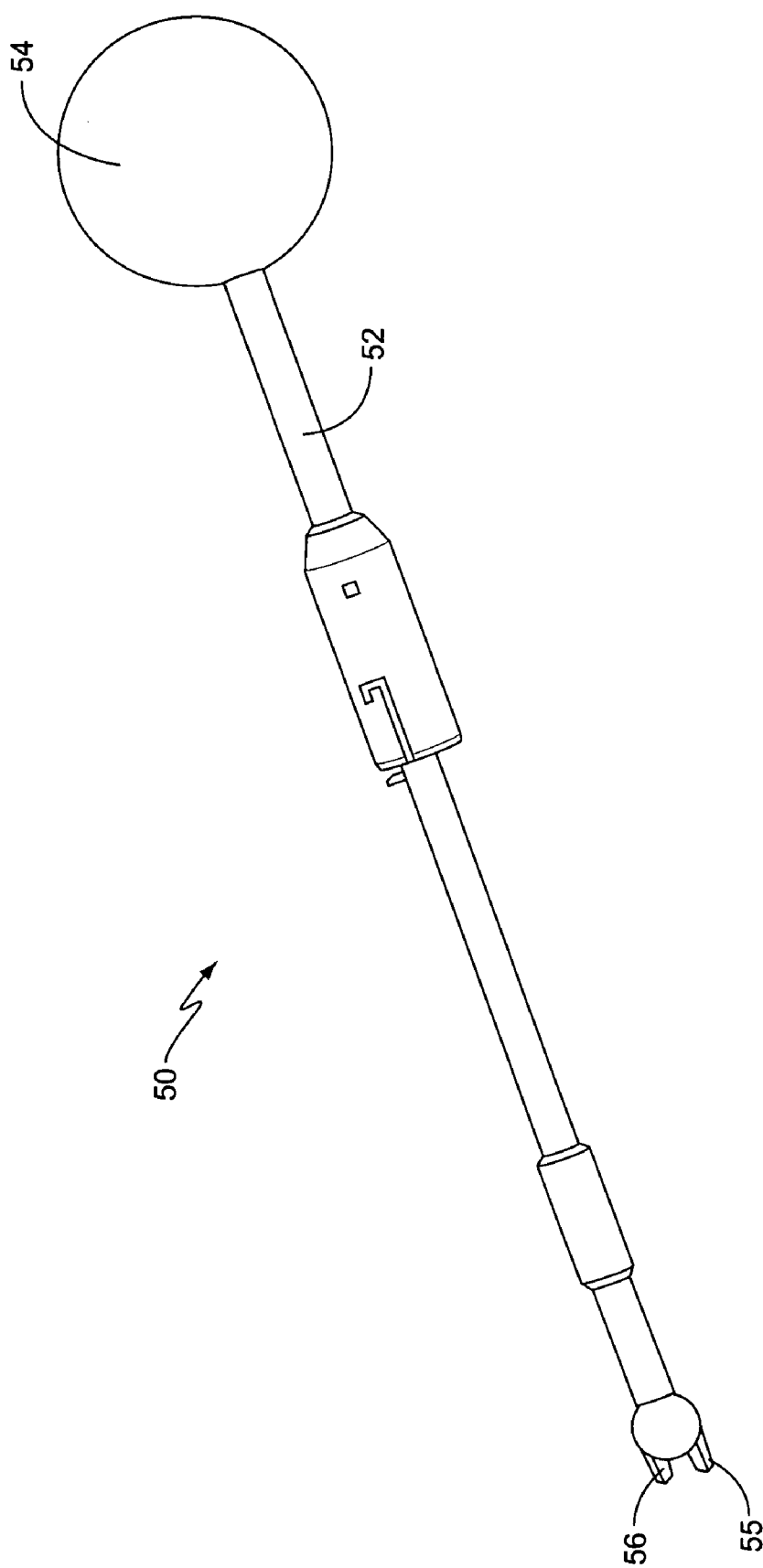
FIG. 17 is a perspective view of an insertion device according to one embodiment of the present invention.

FIG. 17 illustrates one embodiment of the insertion device 50 for inserting the spacer 10 into the intervertebral space between the vertebral members 99. The insertion device 50 includes a first elongated member 51 movably attached to a second elongated member 52. The second elongated member 52 includes a handle 54 mounted on a proximal end that is grasped and manipulated by the physician. A receiver connector 55 extends outward from a distal end of the first member 51. The receiver connector 55 is threaded to mate with the threads on the receiver opening 31 and attach the spacer 10 to the insertion device 50. The first member 51 includes the anti-rotation connector 56 on a distal end. The first member 51 is movable along the second member 52 between an engaged position with the connector 56 in contact with the anti-rotation feature 32, and a disengaged position with the connector 56 spaced from the anti-rotation feature 32. In one embodiment, the rotation connector 56 includes a pin that fits within a dimple that forms the anti-rotation feature 32.

In use, the receiver connector 55 is threaded into the receiver opening 31 of the spacer 10 while exterior to the body. The spacer 10 is then inserted into the body by the physician who grasps the handle 54. Once the spacer 10 is in position between the vertebral members 99, the first member 51 is slid down the second member 52 to the engaged position with the pin 32 positioned within the dimple that forms the anti-rotation feature 32. The handle 54 is then rotated to rotate the receiver connecter 55 and unscrew it from the receiver opening 31. The contact of the connector 56 within the anti-rotation feature 32 prevents the entire spacer 10 from rotating. Once unthreaded, the insertion device 50 is removed with the spacer 10 remaining within the body.

FIG. 18 illustrates another embodiment of a receiver opening 31. This embodiment features a tapered opening with the receiver connector 55 having a corresponding tapered configuration. The receiver connector 55 can be inserted within the opening 31 with the taper acting as a lock to connect the two members together. In one embodiment, the connector 55 is positioned within the opening 31 and placed within the patient. The handle 54 is tapped with a mallet to unseat the connector 55 to remove the insertion device 50 from the patient while leaving the spacer 10. FIG. 19 illustrates an embodiment with a tapered receiver connector 55 and a pair of anti-rotation arms 56. The arms 56 have a distal end that conforms with the exterior of the first section 20. The arms 56 can be moved outward relative to the receiver connector 55 for the distal ends to contact the first section 20 and apply a force to disconnect the tapered receiver connector 55 from the opening 31.

FIG. 20 illustrates another embodiment with indents 39 positioned within the opening 31. For use with this embodiment, the connector 55 includes ball detents that fit within the indents 39 to lock the insertion device 50 to the spacer 10.

FIG. 21 illustrates an embodiment for use with an insertion device 50 having a co-axial receiver connector 55 and anti-rotation connector 56. A first section 31 a of opening is sized to receive one of the connectors 55, 56, and a second section 31b sized to receive the other connector. Connector 55 may be interior or exterior to connector 56. The sections 31a, 31b may be polygonal in shape, such as a hexagonal, may be threaded, or a combination of both.

In another embodiment, the receiver connector 55 comprises arms that are movable between an extended position that extend outward from the first member 51 and a retracted position with the arms in proximity to the first member 51. The handle 54 is movable to selectively position the arms in the extended position with the arms being pressed against the receiver opening 31 to attach the spacer 10. Once inserted and properly positioned, the handle 54 is actuated and the arms are moved to the retracted position and the insertion device 50 can be removed from the spacer 10. In this embodiment, an anti-rotation device 32 is not necessary and the attachment means 30 comprises the receiver 31.

Other devices for attachment of the insertion device 50 include snap fit, cam lock, interference hex, ball release mechanism. The attachment feature 30 may comprise a variety of embodiments, including drilled opening, notch, groove, tab, roughened surface, splines, and suction or gripping feature.

While the illustrative embodiments discussed above have assumed that the member 50 replaces a single intervertebral disc, the present invention also encompasses situations where the member 50 replaces more than one intervertebral disc—a so-called corpectomy construct. This can be achieved through the use of a larger member 50, or by multiple members 50 that can be attached and detached from the device 10.

Additionally, although the devices and methods illustrated and described above are particularly useful in treating the lumbar region of the spine, it should nevertheless be understood that the present invention is also applicable to other portions of the spine, including the cervical, thoracic, and sacro-iliac regions.

The term "vertebral member" and the like are used generally to describe the vertebral geometry comprising the vertebral body, pedicles, lamina, and processes. Likewise, the term "intervertebral space" and the like are used generally to describe the space between vertebral members. The intervertebral space may be formed between adjacent vertebral members, or between non-adjacent vertebral members. The spacer 10 may be sized and shaped, and have adequate strength requirements to be used within the different regions of the spine.

The embodiment of FIGS. 1 and 2 illustrate the first section 20 having a substantially flat section opposite from the second section 21. In one embodiment, the attachment feature 30 is positioned within this flat section. In other embodiments, the first section 20 does not include a flat section and the may not include a substantially flat section.

The term "spacer 10" is used herein in a general sense to describe a device that is positioned between vertebral members 99. In one embodiment, the spacer 10 is an implant that remains within the body. In another embodiment, the spacer 10 is a jig which is a fixture or device to guide or hold a cutting, measuring, or space maintaining device in order to prepare a location, such as a vertebral member or intervertebral space, in order to receive an implant. In these embodiments, the spacer 10 may be removed from the body at the completion of the procedure.

Figure 4:
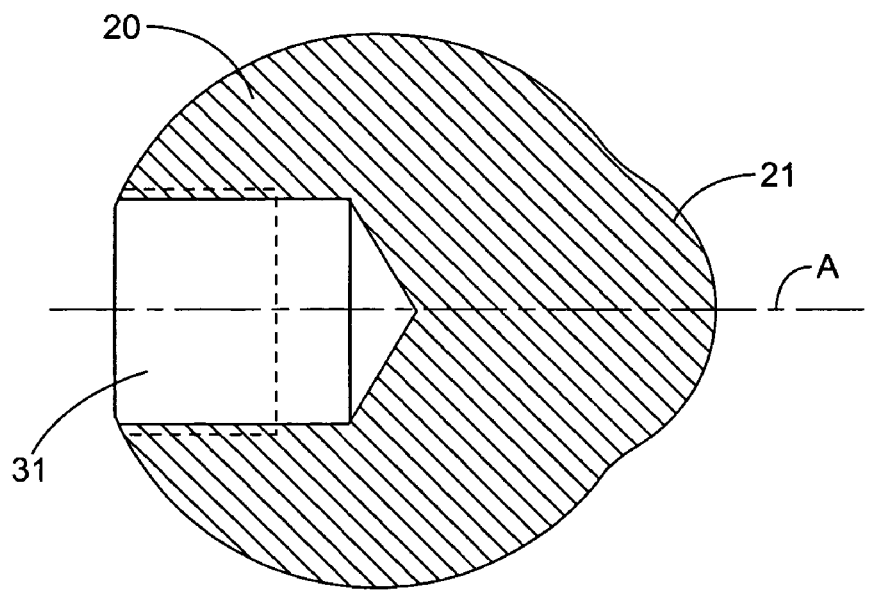
FIG. 4 is a cross-sectional view of the spacer cut along line A-A of FIG. 3.

Other embodiments of the present invention may be carried out in other specific ways than those herein set forth without departing from the scope and essential characteristics of the invention. The terms "upper", "lower", "inner", "outer", and the like are terms to describe the relative positioning of different elements, and are used in a general sense. The spacer 10 may be solid as illustrated in FIG. 4, or have a hollow interior. Receiver opening 31 may include threads or have no threads, and may be of different sizes, varying diameters, and different shapes (e.g., circular, rectangular). The present embodiments are, therefore, to be considered in all respects as illustrative and not restrictive, and all changes coming within the meaning and equivalency range of the appended claims are intended to be embraced therein.

What is claimed is:

1. An intervertebral device for implantation between two adjacent vertebral bodies comprising:
    a first spherical section having a first radius and a first exterior spherical surface, the first section configured for directly contacting the vertebral bodies; and
    a second section extending outward from a first side of the first spherical section in a substantially tangent manner, the second section having a second exterior surface, the second section capable of directly contacting the vertebral bodies;
    a receiver opening positioned within the first spherical section and located opposite from the second section;

the first spherical section and the second section being in an overlapping arrangement and forming an elongated, non-spherical shape;

the first exterior spherical surface comprising a majority of a total exterior surface of the device.

2. The device of claim 1, wherein the second section comprises:

a proximal section that is a transition section extending outward from the first section; and a distal portion, wherein the second exterior surface of the distal portion is defined by a second radius, the second radius being smaller than the first radius.

3. The device of claim 1, wherein a center point of the first spherical section is positioned along a longitudinal centerline of the device.

4. The device of claim 3, wherein a second section center point is positioned along the longitudinal centerline of the device.

5. The device of claim 1, wherein the first spherical section comprises an anterior section of the device.

6. The device of claim 1, further comprising an attachment means positioned within the first spherical section and located between superior and inferior surfaces of the device.

7. The device of claim 1, wherein the receiver opening is threaded.

8. The device of claim 1, wherein the receiver opening is centered along longitudinal and lateral centerlines.

9. The device of claim 1, further comprising an anti-rotation feature positioned adjacent to the receiver opening and located between superior and inferior surfaces of the device.

10. The device of claim 9, wherein the anti-rotation feature comprises a dimple that extends into the first spherical section.

11. The device of claim 9, wherein the anti-rotation feature is positioned along a lateral centerline of the device.

12. An intervertebral device for implantation between two adjacent vertebral bodies comprising:

a first section having a first exterior surface, a majority of the first exterior surface coinciding with a first segment of a first sphere that includes a first radius and a first center point on a longitudinal centerline of the device, the first exterior surface configured for directly contacting the vertebral bodies;

a second section in overlapping arrangement with the first section, the second section having a second exterior surface that extends from the first surface in a substantially tangent manner, a portion of the second exterior surface coinciding with a second segment of a second sphere that includes a second radius and a second center point on the longitudinal centerline, the second exterior surface capable of directly contacting the vertebral bodies;

first and second openings that are spaced apart and each extend into the first section along the first exterior surface that coincides with the first segment of the sphere, at least one of the first and second openings being on an opposite side of the first section from the second section;

the second segment intersecting the longitudinal centerline and the second center point spaced a distance apart from the first center point, the distance being less than the sum of the first and second radii; and the first and second exterior surfaces being merged together forming an overall non-spherical shape.

13. The device of claim 12, wherein one of the first and second openings is centered along the longitudinal centerline.

14. An intervertebral device for positioning between vertebral members, the device comprising:

a first spherical section with a first exterior spherical surface, the first spherical surface configured for directly contacting the vertebral members;

a second spherical section with a second exterior spherical surface and extending outward from a side of the first section in a substantially tangent manner, the first and second spherical sections being merged to form an elongated shape with a total exterior surface, a majority of the total exterior surface being formed by the first exterior spherical surface, the second exterior spherical surface capable of directly contacting the vertebral members; and an attachment feature positioned on the first section opposite from the second section;

the device having an elongated, non-spherical overall shape when positioned between the vertebral members for the attachment feature to be spaced from the vertebral members.

15. An intervertebral device to position between vertebral members, the device comprising:

a first section having an exterior surface and a volume, a majority of the exterior surface coinciding with a sphere centered on a longitudinal axis of the device, the first exterior surface configured for directly contacting the vertebral members;

a second section extending outward in a first direction from the first section in a substantially tangent manner, the second section capable of directly contacting the vertebral members;

an attachment feature positioned in the first section opposite from the second section;

an anti-rotation feature co-axially aligned with the attachment feature;

the device having a total volume and a total exterior surface, the volume of the first section comprising a majority of the total volume of the device and the exterior surface of the first section comprising a majority of the total exterior surface of the device;

the second section extending outward a distance to minimize movement of the first section to maintain the attachment feature spaced from the vertebral members.

16. The device of claim 15, wherein the first section is substantially spherical.

* * * * *